(12) United States Patent
Roche et al.

(10) Patent No.: US 8,183,265 B2
(45) Date of Patent: May 22, 2012

(54) 2-ADAMANTYL-BUTYRAMIDE DERIVATIVES AS SELECTIVE 11β-HSD1 INHIBITORS

(75) Inventors: Didier Roche, Saclay (FR); Denis Carniato, Marcoussis (FR); Liliane Doare, Vitry-Chatillon (FR); Christine Charon, Gometz-le-Chatel (FR); Caroline Leriche, Paris (FR)

(73) Assignee: Merck Patent GmbH, Darmstadt (DE)

( * ) Notice: Subject to any disclaimer, the term of this patent is extended or adjusted under 35 U.S.C. 154(b) by 123 days.

(21) Appl. No.: 12/520,141

(22) PCT Filed: Nov. 22, 2007

(86) PCT No.: PCT/EP2007/010124
§ 371 (c)(1),
(2), (4) Date: Jun. 19, 2009

(87) PCT Pub. No.: WO2008/074384
PCT Pub. Date: Jun. 26, 2008

(65) Prior Publication Data
US 2010/0022597 A1  Jan. 28, 2010

(30) Foreign Application Priority Data
Dec. 21, 2006  (EP) .................................. 06292011

(51) Int. Cl.
| A01N 43/80 | (2006.01) |
| A01N 43/40 | (2006.01) |
| A61K 31/42 | (2006.01) |
| A61K 31/44 | (2006.01) |
| C07D 261/00 | (2006.01) |
| C07D 413/00 | (2006.01) |
| C07D 413/04 | (2006.01) |

(52) U.S. Cl. ..................... 514/340; 514/380; 546/269.4; 548/244

(58) Field of Classification Search ................... 514/340, 514/380; 546/269.4; 548/244
See application file for complete search history.

(56) References Cited

U.S. PATENT DOCUMENTS
7,217,838 B2 * 5/2007 Rohde et al. ................. 564/192
2006/0281773 A1  12/2006 Patel et al.

FOREIGN PATENT DOCUMENTS
| WO | WO 2004/056744 | * | 7/2004 |
| WO | WO 2005/095353 | * | 10/2005 |
| WO | WO 2006/024627 A2 | | 3/2006 |
| WO | WO 2006/024628 A1 | | 3/2006 |
| WO | WO 2006/048750 A2 | | 5/2006 |
| WO | WO 2006/074244 A2 | | 7/2006 |
| WO | WO 2007/050612 | * | 5/2007 |

OTHER PUBLICATIONS

Lapinsh, et al., Proteochemometric Mapping of the Interaction of Organic Compounds with Melanocortin Receptor Subtypes, Mol. Pharmacol., vol. 67, No. 1, 50-59 (2005).*
Saito, et al., Lower Rim Runctionalized Resorcinarenes: Useful Modules for Supramolecular Chemistry, Organic Letters, 1(8), 1241-44 (1999).*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Andrews, et al., Abnormal Cortisol Metabolism and Tissue Sensitivity to Cortisol in Patients with Glucose Intolerance, The Journal of Clinical Endocrinology & Metabolism 87 (12), 5587-5593 (2002).*
Saito, et al., Lower Rim Functionalized Resorcinarenes: Useful Modules for Supramolecular Chemistry, Organic Letters, 1(8), 1241-44 (1999).*
International Search Report of PCT/EP2007/010124 (Jan. 16, 2008).
Database Chemcats [Online] Chemical Abstracts Service—XP002432638 (Aug. 1, 2005).
Database Chemcats [Online] Chemical Abstracts Service—XP002432639 (Feb. 9, 2007).
Database Chemcats [Online] Chemical Abstracts Service—XP002432641 (Feb. 9, 2007).

* cited by examiner

Primary Examiner — Andrew D Kosar
Assistant Examiner — Erich A Leeser
(74) Attorney, Agent, or Firm — Millen, White, Zelano & Branigan, P.C.

(57) ABSTRACT

The present invention relates to 2-adamantyl-butyramide derivatives of formula I as selective inhibitors of the enzyme 11-beta-hydroxysteroid dehydrogenase type 1 (11β-HSD-1) and the use of such compounds for the treatment and prevention of metabolic syndrome, diabetes, insulin resistance, obesity, lipid disorders, glaucoma, osteoporosis, cognitive disorders, anxiety, depression, immune disorders, hypertension and other diseases and conditions.

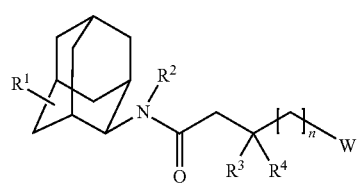

14 Claims, No Drawings

2-ADAMANTYL-BUTYRAMIDE DERIVATIVES AS SELECTIVE 11β-HSD1 INHIBITORS

FIELD OF THE INVENTION

The present invention relates to 2-adamantyl-butyramide derivatives as selective inhibitors of the enzyme 11-beta-hydroxysteroid dehydrogenase type 1 (11β-HSD-1) and the use of such compounds for the treatment and prevention of metabolic syndrome, diabetes, insulin resistance, obesity, lipid disorders, glaucoma, osteoporosis, cognitive disorders, anxiety, depression, immune disorders, hypertension and other diseases and conditions.

BACKGROUND OF THE INVENTION

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268: 4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is widely expressed in liver, adipose tissue, brain, lung and other glucocorticoid tissue, while the isoform 2 (11β-HSD2) expression is limited to tissues that express the mineralocorticoid receptor, such as kidney, gut and placenta. Then the inhibition of 11β-HSD2 is associated with serious side effects, such as hypertension.

Excess cortisol is associated with numerous disorders, including diabetes, obesity, dyslipidemia, insulin resistance and hypertension. The administration of 11β-HSD1 inhibitors decreases the level of cortisol and other 11β-hydroxysteroids in target tissues, thereby reducing the effects of excessive amounts of cortisol and other 11β-hydroxysteroids. Thus, 11β-HSD1 is a potential target for therapy associated with numerous disorders that may be ameliorated by reduction of glucocorticoid action. Therefore, the inhibition of 11β-HSD1 can be used to prevent, treat or control diseases mediated by abnormally high levels of cortisol and other 11β-hydroxysteroids, such as diabetes, obesity, hypertension or dyslipidemia. Inhibition of 11β-HSD1 activity in the brain such as to lower cortisol levels may also be useful to treat or reduce anxiety, depression, cognitive impairment or age-related cognitive dysfunction (Seckl, et al., Endocrinology, 2001, 142: 1371-1376).

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing type 2 diabetes in the presence of abnormally high levels of cortisol (Long et al., J. Exp. Med. 1936, 63: 465-490; Houssay, Endocrinology 1942, 30: 884-892). In addition, it has been well substantiated that 11β-HSD1 plays an important role in the regulation of local glucocorticoid effect and of glucose production in the liver (Jamieson et al., J. Endocrinol. 2000, 165: 685-692). In Walker, et al., J. Clin. Endocrinol. Metab. 1995, 80: 3155-3159, it was reported that the administration of the non-specific 11β-HSD1 inhibitor carbenoxolone resulted in improved hepatic insulin sensitivity in humans.

Furthermore, the hypothesized mechanism of action of 11β-HSD1 in the treatment of diabetes has been supported by various experiments conducted in mice and rats. These studies showed that the mRNA levels and activities of two key enzymes in hepatic glucose production, phosphoenolpyruvate carboxykinase (PEPCK) and glucose-6-phosphatase (G6Pase) were reduced upon administration of 11β-HSD1 inhibitors. In addition, blood glucose levels and hepatic glucose production were shown to be reduced in 11β-HSD1 knockout mice. Additional data gathered using this murine knockout model also confirm that inhibition of 11β-HSD1 will not cause hypoglycemia, since the basal levels of PEPCK and G6Pase are regulated independently of glucocorticoids (Kotelevtsev et al., Proc. Natl. Acad. Sci. USA 1997, 94: 14924-14929).

Therefore, the administration of a therapeutically effective amount of an 11β-HSD1 inhibitor is effective in treating, controlling and ameliorating the symptoms of diabetes, especially non-insulin dependent diabetes (NIDDM, type 2 diabetes mellitus) and administration of a therapeutically effective amount of an 11β-HSD1 inhibitor on a regular basis delays or prevents the onset of diabetes, particularly in humans.

The effect of elevated levels of cortisol is also observed in patients who have Cushing's Syndrome, which is a metabolic disease characterized by high levels of cortisol in the blood stream. Patients with Cushing's Syndrome often develop NIDDM.

Excessive levels of cortisol have been associated with obesity, perhaps due to increased hepatic gluconeogenesis. Abdominal obesity is closely associated with glucose intolerance, diabetes, hyperinsulinemia, hypertriglyceridemia and other factors of Metabolic Syndrome, such as high blood pressure, elevated VLDL and reduced HDL (Montague et al., Diabetes, 2000, 49: 883-888). In obese subjects, 11β-HSD-1 activity in adipose tissue is markedly increased and positively correlated with body mass. It has also been reported that inhibition of the 11β-HSD1 in pre-adipocytes (stromal cells) resulted in a decreased rate of differentiation into adipocytes. This is predicted to result in diminished expansion (possibly reduction) of the omental fat depot, which may lead to reduced central obesity (Bujalska et al., Lancet 1997, 349: 1210-1213).

Thus, the administration of an effective amount of an 11β-HSD1 inhibitor is useful in the treatment or control of obesity. Long-term treatment with an 11β-HSD1 inhibitor is also useful in delaying or preventing the onset of obesity, especially if the patient uses an 11β-HSD1 inhibitor in combination with controlled diet end exercise.

By reducing insulin resistance and maintaining serum glucose at normal concentrations, compounds of the present invention also have utility in the treatment and prevention of conditions that accompany type 2 diabetes and insulin resistance, including the Metabolic Syndrome, obesity, reactive hypoglycemia and diabetic dyslipidemia.

Inhibition of 11β-HSD1 in mature adipocytes is expected to attenuate secretion of the plasminogen activator inhibitor 1 (PAI-1), which is an independent cardiovascular risk factor, as reported in Halleux et al., J; Clin. Endocrinol. Metab. 1999, 84: 4097-4105. In addition, a correlation has been shown to exist between glucocorticoid activity and certain cardiovascular risk factors. This suggests that a reduction of the glucocorticoid effects would be beneficial in the treatment or prevention of certain cardiovascular diseases (Walker et al., Hypertension 1998, 31: 891-895; and Fraser et al., Hypertension 1999, 33: 1364 1368).

Since hypertension and dyslipidemia contribute to the development of atherosclerosis and inhibition of 11β-HSD1 activity and a reduction in the amount of cortisol are beneficial in treating or controlling hypertension, administration of a therapeutically effective amount of an 11β-HSD1 inhibitor of the present invention may also be especially beneficial in treating, controlling or delaying the onset of or preventing atherosclerosis.

11β-HSD1 has also been implicated in the process of appetite control and therefore is believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11β-HSD1 in the brain may increase satiety, thus resulting in a decreased food intake (Woods et al., Science 1998, 280: 1378-1383).

Another possible therapeutic effect associated with modulation of 11β-HSD1 is that which is related to various pancreatic aliments. It is reported that inhibition of 11β-HSD1 in murine pancreatic β-cells increases glucose stimulated insulin secretion (Davani et al., J. Biol. Chem. 2000, 275: 34841-34844). This follows from the preceding discovery that glucocorticoids were previously found to be responsible for reduced pancreatic insulin release in vivo (Billaudel et al., Horm. Metab. Res. 1979, 11: 555-560). Thus, it is suggested that inhibition of 11β-HSD1 would yield other beneficial effects in the treatment of diabetes other than the predicted effects on the liver and of fat reduction.

Excessive levels of cortisol in the brain may also result in neuronal loss or dysfunction through the potentiation of neurotoxins. Administration of an effective amount of an 11β-HSD1 inhibitor results in the reduction, amelioration, control or prevention of cognitive impairment associated with aging and of neuronal dysfunction. Cognitive impairment has been associated with aging, and excess levels of cortisol in the brain (see J. R. Seckl and B. R. Walker, Endocrinology, 2001, 142: 1371 1376, and references cited therein). 11β-HSD1 also regulates glucocorticoid activity in the brain and thus contributes to neurotoxicity (Rajan et al., Neuroscience 1996, 16: 65-70; Seckl et al., Necroendocrinol. 2000, 18: 49-99). Stress and/or glucocorticoids are known to influence cognitive function (de Quervain et al., Nature 1998, 394: 787-790), and unpublished results indicate significant memory improvement in rats treated with a non-specific 11β-HSD1 inhibitor. These reports, in addition to the known effects of glucocorticoids in the brain, suggest that inhibiting 11β-HSD1 in the brain may have a positive therapeutic effect against anxiety, depression and related conditions (Tronche et al., Nature Genetics 1999, 23: 99-103). 11β-HSD1 reactivates 11-dehydrocorticosterone to corticosterone in hippocampal cells and can potentiate kinase neurotoxicity, resulting in age-related learning impairments. Therefore, selective inhibitors of 11β-HSD1 are believed to protect against hippocampal function decline with age (Yau et al., Proc Natl. Acad. Sci. USA 2001, 98: 4716-4721). Thus, it has been hypothesized that inhibition of 11β-HSD1 in the human brain would protect against deleterious glucocorticoid-mediated effects on neuronal function, such as cognitive impairment, depression, and increased appetite.

Furthermore, 11β-HSD1 is believed to play a role in immunomodulation based on the general perception that glucocorticoids suppress the immune system. There is known to be a dynamic interaction between the immune system and the HPA (hypothalamic-pituitary-adrenal) axis (Rook, Baillier's Clin. Endocrinol. Metab. 2000, 13: 576-581), and glucocorticoids help balance between cell-mediated responses and humoral responses. Increased glucocorticoid activity, which may be induced by stress, is associated with a humoral response and as such, the inhibition of 11β-HSD1 may result in shifting the response towards a cell-based reaction. In certain disease states, such as tuberculosis, leprosy and psoriasis, and even under conditions of excessive stress, high glucocorticoid activity shifts the immune response to a humoral response, when in fact a cell based response may be more beneficial to the patient. Inhibition of 11β-HSD1 activity and the attendant reduction in glucocorticoid levels on the other hand shifts the immune response toward a cell based response (D. Mason, Immunology Today, 1991, 12: 57-60, and G. A. Vt. Rook, Baillier's Clin. Endocrinol. Metab., 1999, 13: 576-581). It follows then, that an alternative utility of 11β-HSD1 inhibition would be to bolster a temporal immune response in association with immunization to ensure that a cell based response would be obtained.

Recent reports suggest that the levels of glucocorticoid target receptors and of HSDs are connected with the susceptibility to glaucoma (J. Stokes et al., Invest. Ophthalmol. 2000, 41: 1629-1638). Further, a connection between inhibition of 11β-HSD1 and a lowering of the intraocular pressure was recently reported (Walker et al., poster P3-698 at the Endocrine society meeting Jun. 12-15, 1999, San Diego). It was shown that administration of the nonspecific 11β-HSD1 inhibitor carbenoxolone resulted in the reduction of the intraocular pressure by 20% in normal patients. In the eye, 11β-HSD1 is expressed exclusively in the basal cells of the corneal epithelium, the non-pigmented epithelium of the cornea (the site of aqueous production), ciliary muscle, and the sphincter and dilator muscles of the iris. In contrast, the distant isoenzyme 11-hydroxysteroid dehydrogenase type 2 ("11β-HSD2") is highly expressed in the non-pigmented ciliary epithelium and corneal endothelium. No HSDs have been found at the trabecular meshwork, which is the site of drainage. Therefore, 11β-HSD1 is suggested to have a role in aqueous production and inhibition of 11β-HSD1 activity is useful in reducing intraocular pressure in the treatment of glaucoma.

Glucocorticoids also play an essential role in skeletal development and function but are detrimental to such development and function when present in excess. Glucocorticoid-induced bone loss is partially derived from suppression of osteoblast proliferation and collagen synthesis, as reported in C. H. Kim et al., J. Endocrinol. 1999, 162: 371 379. It has been reported that the detrimental effects of glucocorticoids on bone nodule formation can be lessened by administration of carbenoxolone, which is a non-specific 11β-HSD1 inhibitor (C. G. Bellows et al., Bone 1998, 23: 119-125). Additional reports suggest that 11β-HSD1 maybe responsible for providing increased levels of active glucocorticoid in osteoclasts, and thus in augmenting bone resorption (M. S. Cooper et al., Bone 2000, 27: 375-381). This data suggests that inhibition of 11β-HSD1 may have beneficial effects against osteoporosis via one or more mechanisms which may act in parallel.

11β-HSD1 inhibitors are known e.g. from the WO0410629, WO03065983, WO04089896, WO04089380, WO04065351, WO04033427 or WO04041264. However, 2-adamantyl-butyramide derivatives are not disclosed as active 11β-HSD1 inhibitors.

2-adamantyl amide derivatives are disclosed for example in WO05014529, WO0043354, WO05102332, WO05102331, WO03045367, WO0192229, WO03092679 and in Dothager R. S. et al. (J. Am. Chem. Soc. Jun. 22, 2005: 127(24):8686-96). The disclosure of these publications, however, does not encompass the 2-adamantyl-butyramide derivatives of the present invention nor the use of the disclosed compounds as 11β-HSD1 inhibitors.

Further 2-adamantyl derivatives are disclosed for example in WO06050908, WO06049952, WO06050907, WO04089470, WO04056744, WO04056745 WO05108359, US2005277647, US2005261302, US2005245533, US2005245532 and WO05108368 as 11β-HSD1 inhibitors. The disclosure of these publications, however, does not encompass the 2-adamantyl-butyramide derivatives of the present invention as 11β-HSD1 inhibitors.

Thus, as there remains a continuing need in advantageous therapeutics, a preferred object of the present invention was to provide new pharmaceutically active compounds for the treatment of diseases such as diabetes, obesity, glaucoma, osteoporosis, cognitive disorders, immune disorders, depression, hypertension, and others.

The citation of any reference in this application is not an admission that the reference is prior art to this application.

SUMMARY OF THE INVENTION

Surprisingly, it was found that the compounds of the present invention are very active 11β-HSD1 inhibitors. Therefore, an embodiment of the present invention are compounds of the formula I,

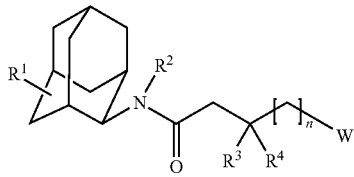

I wherein, the adamantyl residue is mono-, di- or trisubstituted by $R^1$ and
$R^1$ is H, A, Ar, heteroaryl, cycloalkyl, alkyloxy, aryloxy, Hal, $OR^7$, $SR^7$, $N(R^7)_2$, $NO_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $COAr$, $SO_2NH_2$, $OSO_3R^7$, $SO_2R^7$, $SO_3R^7$, $SO_2N(R^7)_2$, $OCOR^7$ or $OCON(R^7)_2$,
$R^2$ is H or A,
$R^3$, $R^4$ are independently from each other H, Hal, $C_1$-$C_4$-alkyl or $C_1$-$C_4$-alkyloxy, or $R^3$, $R^4$ and the C to which they are attached form a $C_3$-$C_9$-cycloalkyl or a $C_3$-$C_9$-cycloalkyloxy, and $R^3$, $R^4$ or the cycloalkylic or cycloalkyloxic ring are optionally mono-, di- or trisubstituted by $R^5$ or $R^6$,
W is Ar, heteroaryl, aryloxy, alkoxy or thioaryl, optionally mono-, di- or trisubstituted by $R^5$ or $R^6$ or W is selected form the group consisting of $COOR^5$, $COR^5$, $CHOHR^5$, $SO_2R^5$, $SO_2NR^5R^6$, $CO_2NR^5R^6$ and $CONR^5R^6$,
$R^5$, $R^6$ are independently from each other H, A, Ar, heteroaryl, cycloalkyl, alkyloxy, aryloxy, Hal, $OR^7$, $SR^7$, $N(R^7)_2$, $NO_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $COAr$, $SO_2NH_2$, $OSO_3R^7$, $SO_2R^7$, $SO_3R^7$ or $SO_2N(R^7)_2$,
$R^7$ H or alkyl, wherein optionally 1-7 H-atoms are substituted by Hal,
n is 1 or 2,
m 0, 1, 2, 3, 4 or 5,
and the physiologically acceptable salts, derivatives, prodrugs, solvates and stereoisomers thereof, including mixtures thereof in all ratios.

If the adamantyl residue is di- or trisubstituted by $R^1$, the two or three substituents can be equal or different and are selected independently form each other from the group consisting of H, A, Ar, heteroaryl, cycloalkyl, alkyloxy, aryloxy, Hal, $OR^7$, $SR^7$, $N(R^7)_2$, $NO_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $COAr$, $SO_2NH_2$, $OSO_3R^7$, $SO_2R^7$, $SO_3R^7$, $SO_2N(R^7)_2$, $OCOR^7$ and $OCON(R^7)_2$.

A preferred embodiment of the present invention are compounds according to formula I, wherein W is $CONR^5R^6$, oxadiazolyl or phenoxy substituted by $R^5$ and $R^6$, and the physiologically acceptable salts, derivatives, prodrugs, solvates and stereoisomers thereof, including mixtures thereof in all ratios.

A preferred embodiment of the present invention are compounds according to formula I, wherein $R^3$, $R^4$ are independently from each other Hal or methyl, or $R^3$, $R^4$ and the C to which they are attached form a cyclopentyl or cycohexyl,
and the physiologically acceptable salts, derivatives, prodrugs, solvates and stereoisomers thereof, including mixtures thereof in all ratios.

A further preferred embodiment of the present invention are compounds according to formula I, wherein $R^1$ is H, Hal, $OR^7$, $SR^7$, $N(R^7)_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $SO_2NH_2$, $OSO_3R^7$, $SO_2R^7$, $SO_3R^7$, $SO_2N(R^7)_2$, $OCOR^7$ or $OCON(R^7)_2$, and the physiologically acceptable salts, derivatives, prodrugs, solvates and stereoisomers thereof, including mixtures thereof in all ratios.

A further preferred embodiment of the present invention are compounds according to formula I, wherein $R^2$ is H or Me, and the physiologically acceptable salts, derivatives, prodrugs, solvates and stereoisomers thereof, including mixtures thereof in all ratios.

A further preferred embodiment of the present invention are compounds according to formula I, wherein
$R^1$ is H, Hal, $OR^7$, $SR^7$, $N(R^7)_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $SO_2NH_2$, $OSO_3R^7$, $SO_2R^7$, $SO_3R^7$, $SO_2N(R^7)_2$, $OCOR^7$ or $OCON(R^7)_2$,
$R^2$ is H or Me,
$R^3$, $R^4$ are independently from each other Hal or methyl, or $R^3$, $R^4$ and the C to which they are attached form a cyclopentyl or cycohexyl,
W is $CONR^5R^6$, oxadiazolyl or phenoxy substituted by $R^5$ and $R^6$,
and the physiologically acceptable salts, derivatives, prodrugs, solvates and stereoisomers thereof, including mixtures thereof in all ratios.

Another especially preferred embodiment of the present invention are compounds according to formula I, selected from the group consisting of
a) N-Adamantan-2yl-2-[1-(isobutylcarbamoyl-methyl)-cyclopentyl-acetamide
b) 4-(Adamantan-2-ylcarbamoyl)-3,3-dimethyl-butyric acid
c) [1-(Adamantan-2-ylcarbamoylmethyl)-cyclopentyl]-acetic acid
d) [1-(Adamantan-2-ylcarbamoylmethyl)-cyclohexyl]-acetic acid
e) 2-[1-(Adamantan-2-ylcarbamoylmethyl)-cyclopentyl]-N-(4-fluoro-phenyl)-acetamide
f) 2-[1-(Adamantan-2-ylcarbamoylmethyl)-cyclopentyl]-N-benzyl-N-methyl-acetamide
g) 2-[1-(Adamantan-2-ylcarbamoylmethyl)-cyclopentyl]-N-(2-methoxy-phenyl)-acetamide
h) 2-[1-(Adamantan-2-ylcarbamoylmethyl)-cyclopentyl]-N-(4-methoxy-phenyl)-acetamide
i) 2-[1-(Adamantan-2-ylcarbamoylmethyl)-cyclopentyl]-N-(4-fluoro-benzyl)-acetamide j) 2-[1-(Adamantan-2-ylcarbamoylmethyl)-cyclopentyl]-N-pyridin-2-ylmethyl-acetamide
k) 2-[1-(Adamantan-2-ylcarbamoylmethyl)-cyclopentyl]-N-thiazol-2-yl-acetamide
l) 2-[1-(Adamantan-2-ylcarbamoylmethyl)-cyclopentyl]-N-isobutyl-acetamide
m) 2-[1-(Adamantan-2-ylcarbamoylmethyl)-cyclopentyl]-N-cyclopropyl-acetamide
n) N-Adamantan-2-yl-2-[1-(2-oxo-2-pyrrolidin-1-yl-ethyl)-cyclopentyl]-acetamide
o) {1-[(5-Hydroxy-adamantan-2-ylcarbamoyl)-methyl]-cyclohexyl}-acetic acid
p) 3,3-Dimethyl-pentanedioic acid adamantan-2-ylamide cyclopropylamide
q) 3,3-Dimethyl-5-(4-methyl-piperazin-1-yl)-5-oxo-pentanoic acid adamantan-2-ylamide
r) 5-(4-Ethyl-piperazin-1-yl)-3,3-dimethyl-5-oxo-pentanoic acid adamantan-2-ylamide
s) 3,3-Dimethyl-pentanedioic acid adamantan-2-ylamide piperidin-1-ylamide
t) N-Adamantan-2-yl-2-{1-[2-(4-methyl-piperazin-1-yl)-2-oxo-ethyl]-cyclohexyl}-acetamide
u) N-Adamantan-2-yl-2-{1-[2-(4-ethyl-piperazin-1-yl)-2-oxo-ethyl]-cyclohexyl}-acetamide
v) N-Adamantan-2-yl-2-{1-[2-(4-methyl-piperazin-1-yl)-2-oxo-ethyl]-cyclopentyl}-acetamide
w) N-Adamantan-2-yl-2-{1-[2-(4-ethyl-piperazin-1-yl)-2-oxo-ethyl]-cyclopentyl}-acetamide
x) N-Adamantan-2-yl-2-[1-(piperidin-1-ylcarbamoylmethyl)-cyclopentyl]-acetamide
y) 2-(1-Cyclopropylcarbamoylmethyl-cyclopentyl)-N-(5-hydroxy-adamantan-2-yl)-acetamide
z) 2-(1-Cyclopropylcarbamoylmethyl-cyclopentyl)-N-(5-hydroxy-adamantan-2-yl)-acetamide
aa) N-Adamantan-2-yl-2-(1-cyclopropylcarbamoylmethyl-cyclohexyl)-acetamide
bb) 3,3-Dimethyl-5-((S)-3-methyl-piperidin-1-yl)-5-oxo-pentanoic acid adamantan-2-ylamide
cc) 3,3-Dimethyl-5-((R)-3-methyl-piperidin-1-yl)-5-oxo-pentanoic acid adamantan-2-ylamide
dd) N-Adamantan-2-yl-2-{1-[2-((S)-3-methyl-piperidin-1-yl)-2-oxo-ethyl]-cyclopentyl}-acetamide
ee) N-Adamantan-2-yl-2-{1-[2-((R)-3-methyl-piperidin-1-yl)-2-oxo-ethyl]-cyclopentyl}-acetamide
ff) N-Adamantan-2-yl-2-{1-[2-((S)-3-methyl-piperidin-1-yl)-2-oxo-ethyl]-cyclohexyl}-acetamide
gg) N-Adamantan-2-yl-2-{1-[2-((R)-3-methyl-piperidin-1-yl)-2-oxo-ethyl]-cyclohexyl}-acetamide
hh) 3,3-Dimethyl-pentanedioic acid cyclopropylamide(5-hydroxy-adamantan-2-yl)-amide
ii) N-Adamantan-2-yl-4-(4-chloro-2-methoxy-phenoxy)-3,3-dimethyl-butyramide
jj) N-Adamantan-2-yl-4-(2-chloro-phenoxy)-3,3-dimethyl-butyramide
kk) N-Adamantan-2-yl-4-(2,4-dichloro-phenoxy)-3,3-dimethyl-butyramide
ll) N-Adamantan-2-yl-4-(3-cyclopropyl-[1,2,4]oxadiazol-5-yl)-3,3-dimethyl-butyramide
mm) N-Adamantan-2-yl-4-(3-isopropyl-[1,2,4]oxadiazol-5-yl)-3,3-dimethyl-butyramide
nn) N-Adamantan-2-yl-3,3-dimethyl-4-(3-pyridin-2-yl-[1,2,4]oxadiazol-5-yl)-butyramide
oo) N-Adamantan-2-yl-3,3-dimethyl-4-(3-m-tolyl-[1,2,4]oxadiazol-5-yl)-butyramide
pp) N-Adamantan-2-yl-3,3-dimethyl-4-(3-p-tolyl-[1,2,4]oxadiazol-5-yl)-butyramide
qq) N-Adamantan-2-yl-4-[3-(4-methoxy-phenyl)-[1,2,4]oxadiazol-5-yl]-3,3-dimethyl-butyramide
rr) N-Adamantan-2-yl-4-[3-(4-chloro-phenyl)-[1,2,4]oxadiazol-5-yl]-3,3-dimethyl-butyramide
ss) N-Adamantan-2-yl-2-[1-(3-cyclopropyl-[1,2,4]oxadiazol-5-ylmethyl)-cyclopentyl]-acetamide
tt) N-Adamantan-2-yl-2-[1-(3-isopropyl-[1,2,4]oxadiazol-5-ylmethyl)-cyclopentyl]-acetamide
uu) N-Adamantan-2-yl-2-[1-(3-pyridin-2-yl-[1,2,4]oxadiazol-5-ylmethyl)-cyclopentyl]-acetamide
vv) N-Adamantan-2-yl-2-[1-(3-m-tolyl-[1,2,4]oxadiazol-5-ylmethyl)-cyclopentyl]-acetamide
ww) N-Adamantan-2-yl-2-[1-(3-p-tolyl-[1,2,4]oxadiazol-5-ylmethyl)-cyclopentyl]-acetamide
xx) N-Adamantan-2-yl-2-{1-[3-(4-methoxy-phenyl)-[1,2,4]oxadiazol-5-ylmethyl]-cyclopentyl}-acetamide and the physiologically acceptable salts, derivatives, prodrugs, solvates and stereoisomers thereof, including mixtures thereof in all ratios.

The nomenclature as used herein for defining compounds, especially the compounds according to the invention, is in general based on the rules of the IUPAC-organisation for chemical compounds and especially organic compounds.

The term "hydroxyl" means an OH group.

The terms "Alkyl" or "A", as well as other groups having the prefix "alk", such as alkenyl, alkoxy and alkanoyl, mean carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_3$-$C_{10}$, the term alkyl also includes cycloalkyl groups, and combinations of linear or; branched alkyl chains combined with cycloalkyl structures. When no number of carbon atoms is specified, $C_1$-$C_6$ is intended. Especially preferred $C_1$-$C_4$alkyl. A $C_1$-$C_4$alkyl radical is for example a methyl, ethyl, propyl, isopropyl, butyl, isobutyl, tert-butyl.

The term "alkyloxy" means alkoxy groups of a straight or branched configuration. "$C_1$-$C_4$alkyloxy" means alkoxy groups of a straight or branched configuration having the indicated number of carbon atoms. $C_1$-$C_4$alkyloxy is for example a methoxy, ethoxy, propoxy, isopropoxy and the like.

$C_3$-$C_9$cycloalkyl is a subset of alkyl and is understood as meaning a saturated monocyclic hydrocarbon having 3 to 9 carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined. A $C_4$-$C_8$cycloalkyl radical is for example a cyclobutyl, cyclopentyl, cyclohexyl, cycloheptyl, cyclooctyl.

The term "$C_3$-$C_9$cycloalkyloxy" means alkoxy groups of a cyclic configuration having the indicated number of carbon atoms. $C_3$-$C_9$cycloalkyloxy is for example a cyclopropyloxy, cyclobutyloxy, cyclopentyloxy, cyclohexyloxy, cycloheptyloxy, cyclooctyloxy and the like. A cycloalkyloxy group generally is monocyclic unless stated otherwise. Cycloalkyloxy groups are saturated unless otherwise defined.

The terms "Aryl" o "Ar" mean a mono- or polycyclic aromatic ring system containing carbon ring atoms. The preferred aryls are monocyclic or bicyclic 6-10 membered aromatic ring systems. Examples of "aryl" groups include, but are not limited to phenyl, 2-naphthyl, 1-naphthyl, biphenyl, indanyl as well as substituted derivatives thereof. The most preferred aryl is phenyl.

The term "aryloxy" means alkoxy groups of a mono- or polycyclic aromatic ring system containing carbon ring atoms. Examples of "aryl" groups include, but are not limited to Phenyloxy, 2-naphthyloxy, 1-naphthyloxy, biphenyloxy, indanyloxy as well as substituted derivatives thereof. The most preferred aryloxy is phenyloxy.

"Heteroaryl" means an aromatic or partially aromatic heterocycle that contains at least one ring heteroatom selected from O. S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl triazolyl, tetrazolyl, furanyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoxazolyl, isoindolyl, dihydrobenzothienyl, indolizinyl, cinnolinyl, phthalazinyl, quinazolinyl, naphthyridinyl, carbazolyl, benzdioxinyl benzodioxolyl, quinoxalinyl, purinyl, furazanyl, thiophenyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

The term "Hal" refers to fluorine, chlorine, bromine and iodine. Bromine and fluorine are generally preferred. Fluorine is most preferred, when the halogens are substituted on an alkyl or alkoxy group (e.g. $CF_3$ and $CF_3O$).

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I. Some of the compounds described herein contain olefinic double bonds, and unless specified otherwise, are meant to include both E and Z geometric isomers.

Some of the compounds described herein may exist as tautomers such as keto-enol tautomers. The individual tautomers, as well as mixtures thereof, are encompassed within the compounds of structural formula I.

Compounds of structural formula I may be separated into the individual diastereoisomers by, for example, fractional crystallization from a suitable solvent, for example methanol; or ethyl acetate or a mixture thereof or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

In a different aspect of the invention, a pharmaceutical composition is addressed I comprising a compound in accordance with structural formula I, or a pharmaceutically acceptable salt or solvate thereof, in combination with a pharmaceutically acceptable carrier.

By the term "solvate" is meant a hydrate, an alcoholate, or other solvate of crystallization.

The compounds can be prepared by general method 1, 2 and 3, shown below. In all preparative methods, all starting material is known or may easily prepared from known starting materials.

A further embodiment of the present invention is a method for the preparation of the compounds of the present invention, characterized in that a) (general method 1) an amine of formula II, wherein $R^1$ and $R^2$ are as defined above, is reacted with an anhydride of formula III, wherein $R^3$ and $R^4$ are as defined above, to obtain a carboxylic acid derivative of formula IV, wherein $R^1$, $R^2$, $R^3$ and $R^4$ are as defined above, and to activate said carboxylic acid derivative with standard carbodiimides, followed by treatment with an amine of formula V, wherein $R^5$ and $R^6$ are as defined above,

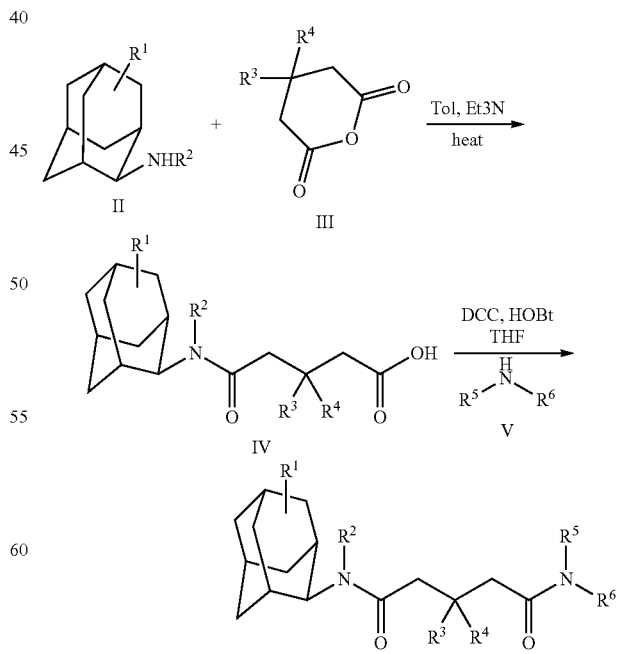

b) (general method 2) a phenol derivative of formula VI, wherein $R^5$ and $R^6$ are as defined above, is reacted with a lactone of formula VII, wherein $R^3$ and $R^4$ are as defined above, under heat to obtain a carboxylic acid derivative of formula IV, wherein $R^3$, $R^4$, $R^5$ and $R^6$ are as defined above, and the respective compound of formula I, wherein $R^1$, $R^2$, $R^3$, $R^4$, $R^5$ and $R^6$ are as defined above, is obtain by amide coupling under standard peptide coupling conditions,

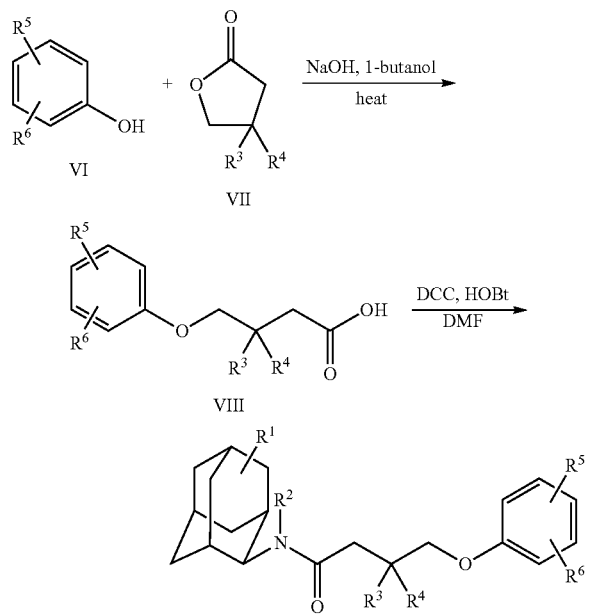

c) (general method 3) a carboxylic acid of formula IV, wherein $R^1$, $R^2$, $R^3$ and $R^4$ are as defined above, is activated and reacted with an amidoxime of formula IX, wherein $R^5$ is as defined above, to obtain an acylamidoxamine of formula X, wherein $R^1$, $R^2$, $R^3$, $R^4$ and $R^5$ are as defined above, and cyclization to a oxadiazole of formula XI, wherein $R^1$, $R^2$, $R^3$, $R^4$ and $R^5$ are as defined above, is obtained by heating said acylamidoxamine in DMF,

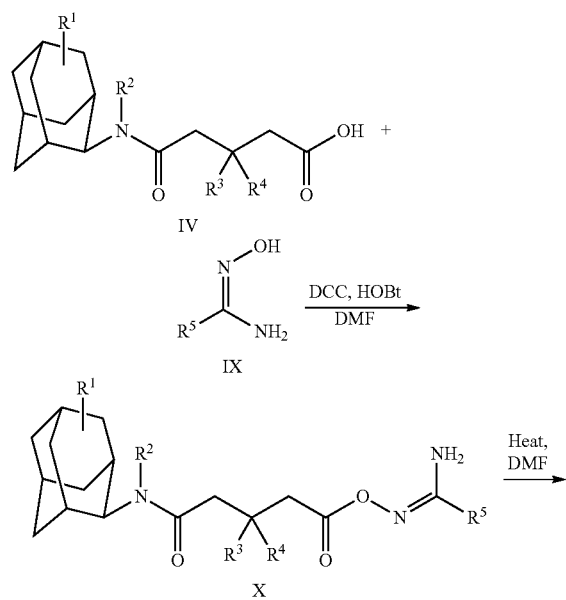

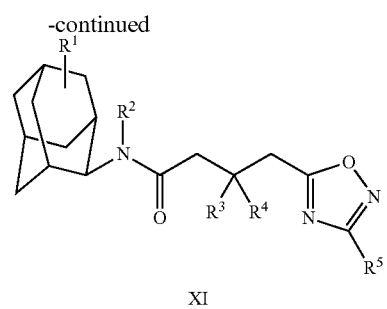

d) a residue $R^1$, $R^2$, $R^3$, $R^4$, $R^5$, $R^6$ and/or $R^7$ as defined above, is converted in another residue $R^1$, $R^2$, $R^3$, $R^4$, $R^5$, $R^6$ and/or $R^7$, e.g. by introducing an alkyl group, or e) a compound of formula I is isolated and/or treated with an acid or a base, to obtain the salt thereof.

All crude products were subjected to standard chromatography using solvent mixtures containing methanol, ethanol, isopropanol, n-hexane, cyclohexane or petrol ether, respectively.

For a further detailed description of the manufacturing processes, please see also the examples and the following general description of the preferred conditions.

A physiologically acceptable salt of a compound according to formula I can also be obtained by isolating and/or treating the compound of formula I obtained by the described reaction with an acid or a base.

The compounds of the formula I and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the formula I. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of the formula I can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono-and-disulfonic acids or laurylsulfuric acid.

Salts with physiologically unacceptable acids, for example picrates, can be used to isolate and/or purify the compounds of the formula I.

On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the formula I can be liberated from their salts by treatment with strong bases, such as sodium hydroxide, potassium hydroxide, sodium carbonate or potassium carbonate, so long as no further acidic groups are present in the molecule In the cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The compounds described herein are selective inhibitors of the 11β-HSD1 enzyme. Thus, the present invention relates to the use of the compounds of the present invention as for inhibiting the reductase activity of 11β-hydroxysteroid dehydrogenase 1, which is responsible for the conversion of cortisone to cortisol.

The 11β-HSD1 inhibitors of structural formula I generally have an inhibition constant IC50 of less than about 500 nM, and preferably less than about 100 nM. Generally, the IC50 ratio 11β-HSD2 to 11β-HSD1 of a compound is at least about two or more, and preferably about ten or greater. Even more preferred are compounds with an IC50 ratio for 11β-HSD2 to 11β-HSD1 of about 20 or greater. For example, compounds of the present invention ideally demonstrate an inhibition constant IC50 against 11β-HSD2 greater than about 1000 nM, and preferably greater than 5000 nM.

The present invention includes the use of an 11β-HSD1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of structural formula I or a pharmaceutically acceptable salt or solvate thereof. Inhibition of the 11β-HSD1 enzyme limits the conversion of cortisone, which is normally inert, to cortisol, which can cause or contribute to the symptoms of these diseases and conditions if present in excessive amounts.

Therefore, a preferred embodiment of the present invention is the use of a compound of the present invention as 11β-HSD1 inhibitor.

A further preferred embodiment of the present invention is the use of a compound of the present invention for the preparation of a medicament.

A further preferred embodiment of the present invention is the use of a compound of the present invention for the preparation of a medicament for the treatment and/or prevention of diseases, which are caused, mediated and/or propagated by high cortisol levels.

A further preferred embodiment of the present invention is the use of a compound of the present invention for the preparation of a medicament for the treatment and/or prevention of one ore more disease or condition selected from the group consisting of metabolic syndrome, diabetes, especially non-insulin dependent diabetes mellitus, prediabetes, insulin resistance, low glucose tolerance, hyperglycemia, obesity and weight-related disorders, lipid disorders such as dyslipidemia, hyperlipidemia, hypertriglyceridemia, hypercholesterolemia, low HDL levels or high LDL levels, glaucoma, osteoporosis, glucocorticoid-mediated effects on neuronal function, such as cognitive impairment, anxiety or depression, neurodegenerative disease, immune disorders such as tuberculosis, leprosy or psoriasis, hypertension, atherosclerosis and its sequelae, vascular restenosis, cardiovascular diseases, pancreatitis, retinopathy, neuropathy and nephropathy.

In another aspect of the invention, a method of treating a condition selected from the; group consisting of: hyperglycemia, low glucose tolerance, insulin resistance, obesity, lipid disorders, dyslipidemia, hyperlipidemia, hypertriglyceridemia, hypercholesterolemia, low MEL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component, in a mammalian patient in need of such treatment is disclosed, comprising administering to the patient a compound in accordance with structural formula I in an amount that is effective to treat said condition.

In another aspect of the invention, a method of delaying the onset of a condition selected from the group consisting of hyperglycemia, low glucose tolerance, insulin resistance, obesity, lipid disorders, dyslipidemia, hyperlipidemia, hypertriglyceridemia, hypercholesterolemia, low EMIL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component in a mammalian patient in need of such treatment is disclosed, comprising administering to the patient a compound in accordance with structural formula I in an amount that is effective to delay the onset of said condition.

A further preferred embodiment of the present invention is a pharmaceutical composition, characterized in that it contains a therapeutically effective amount of one or more compounds according to the invention.

A further embodiment of the present invention is a pharmaceutical composition, characterized in that it further contains one or more additional compounds, selected from the group consisting of physiologically acceptable excipients, auxiliaries, adjuvants, diluents, carriers and pharmaceutically active agents other than the compounds according to the invention.

An additional preferred embodiment of the present invention is a set (kit) consisting of separate packets of
a) a therapeutically effective amount of one or more compounds according to the invention and
b) a therapeutically effective amount one ore more further pharmaceutically active agents other than the compounds according to the invention.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I. Examples of other active ingredients that may be administered in combination with a compound of structural formula I, and either administered separately or in the same pharmaceutical composition, include, but are not limited to: dipeptidyl peptidase IV (DP-IV) inhibitors; insulin sensitizing agents including PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and biguanides, such as metformin and phenformin; insulin or insulin mimetics; sulfonylureas and other insulin secretagogues such as tolbutamide, glipizide, meglitinide and related materials; α-glucosidase inhibitors, such as acarbose; glucagon receptor antagonists such as those disclosed in WO 98/04528, WO 99/01423, WO 00/39088 and WO 00/69810; GLP-1, GLP-1 analogs, and GLP-1 receptor agonists such as those disclosed in WOOO/42026 and WOOO/59887; GIP, GIP mimetics such as those disclosed in WOOO/58360, and GIP receptor agonists; PACAP, PACAP mimetics, and PACAP receptor 3 agonists such as those disclosed in WO 01/23420; cholesterol lowering agents such as HMG-CoA reductase inhibitors (lovastatin, simvastatin, pravastatin, cerivastatin, fluvastatin, atorvastatin, itavastatin, rosuvastatin, and other stating), bile-acid sequestrants (cholestyramine, colestipol, and dialkylaminoalkyl derivatives of a cross-linked dextran), nicotinyl alcohol, nicotinic acid or a salt thereof, inhibitors of cholesterol absorption, such as ezetimibe and beta-sitosterol, acyl CoA:cholesterol acyltransferase inhibitors, such as, for example, avasimibe, and anti-oxidants, such as probucol; PPARδ agonists, such as those disclosed in WO97/28149; antiobesity compounds such as fenfluramine, dextenfluramine, phentermine, sibutramine, orlistat, neuropeptide Y1 or Y5 antagonists, CB 1 receptor inverse agonists and antagonists, adrenergic receptor agonists, melanocortin-receptor agonists, in particular melanocortin-4 receptor agonists, ghrelin antagonists, and melanin-concentrating hormone (MCH) receptor antagonists; ileal bile acid transporter inhibitors; agents intended for use in inflammatory conditions other than glucocorticoids, such as aspirin, non-steroidal anti-inflammatory drugs, azulfidine, and selective cyclooxygenase-2 inhibitors; protein tyrosine phosphatase 1B (PTP-1B) inhibitors; antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telnisartan, and valsartan; and inhibitors of cholesteryl ester transfer protein (CETP). The above combinations include a compound of structural formula I, or a pharmaceutically acceptable salt or solvate thereof, with one or more other active compounds. Non limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

In another aspect of the invention, a method of reducing the risk of developing a condition selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component in a mammalian patient in need of such treatment is disclosed, comprising administering to the patient a compound in accordance with structural formula I in an amount that is effective to reduce the risk of developing said condition.

In another aspect of the invention, a method of treating a condition selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component, in a mammalian patient in need of such treatment, comprising administering to the patient an effective amount of a compound as defined in structural; formula I and a compound selected from the group consisting of: dipeptidyl peptidase-IV (DP-IV); inhibitors; insulin sensitizing agents selected from the group consisting of PPARγ agonists, PPARα agonists, PPARα/γ dual agonists, and biguanides; insulin and insulin mimetics; sulfonylureas and other insulin secretagogues; α-glucosidase inhibitors; glucagon receptor antagonists; GLP-1, GLP-1 analogs, and GLP-1 receptor agonists; GIP, GIP mimetics, and GIP receptor agonists; PACAP, PACAP mimetics, and PACAP receptor 3 agonists; cholesterol lowering agents selected from the group consisting of HMG-CoA reductase inhibitors, sequestrants, nicotinyl alcohol, nicotinic acid and salts thereof, inhibitors of cholesterol absorption, acyl CoA:cholesterol acyltransferase inhibitors, and anti-oxidants; PPARγ agonists; antiobesity compounds; ileal bile acid transporter inhibitors; anti-inflammatory agents, excluding glucocorticoids; protein tyrosine phosphatase 1B (PTP-1B) inhibitors; and antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition. Dipeptidyl peptidase-IV inhibitors that can be combined with compounds of structural formula I include those disclosed in WO 03/004498, WO 03/004496; EP 1 258 476; WO 02/083128; WO 02/062764; WO 03/00025; WO 03/002530; WO 03/002531; WO 03/002553; WO 03/002593; WO 03/000180; and WO 03/000181. Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide Y1 or Y5 antagonists, cannabinoid CB 1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," Expert Opin. Ther. Patents, 11: 1677-1692 (2001) and D. Spanswick and K. Lee, "Emerging antiobesity drugs," Expert Opin. Emerging Drugs, 8: 217-237 (2003).

Neuropeptide Y5 antagonists that can be combined with compounds of structural formula I include those disclosed in U.S. Pat. No. 6,335,345 and WO 01/14376; and specific compounds identified as GW59884A; GW569180A; LY366377; and COP-71683A.

Cannabinoid CB 1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of formula I include those disclosed in WO 03/009847; WO 021068388; WO 99/64002; WO 00/74679; WO 01/70708; and WO 01/70337 as well as those disclosed in J. D. Speake et al., "Recent advances in the development of melanocortin-4 receptor agonists, Expert Opin. Ther. Patents, 12: 1631-1638 (2002).

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of a compound as defined in structural formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HAL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in structural formula I and an HMG-CoA reductase inhibitor.

In another aspect of the invention, a method for delaying the onset or reducing the risk of; developing atherosclerosis in a human patient in need of such treatment is disclosed comprising administering to said patient an effective amount of a compound as defined in structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of I developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-CoA reductase inhibitor is a statin and the cholesterol absorption inhibitor is ezetimibe.

In another aspect of the invention, a pharmaceutical composition is disclosed which comprises a compound according to structural formula I, a compound selected from the group consisting of: DP-IV inhibitors; insulin I sensitizing agents selected from the group consisting of PPARα agonists; PPARγ agonists, PPARα/γ dual agonists, and biguanides; insulin and insulin mimetics; sulfonylureas and other insulin secretagogues; oc-glucosidase inhibitors; glucagon receptor antagonists; GLP-1, GLP-1 analogs, and GLP-1 receptor agonists; GIP, GIP mimetics, and GIP receptor agonists; PACAP, PACAP mimetics, and PACAP receptor 3 agonists; cholesterol lowering agents selected from the group consisting of HMG-CoA reductase inhibitors, sequestrants, (nicotinyl alcohol, nicotinic acid or a salt thereof, inhibitors of cholesterol absorption, acyl CoA:cholesterol acyltransferase inhibitors, and anti-oxidants; PPARδ agonists; antiobesity compounds; ileal bile acid transporter inhibitors; anti-inflammatory agents other than glucocorticoids; protein tyrosine phosphatase 1B (PTP-1B) inhibitors; and antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; inhibitors of cholesteryl ester transfer protein (CETP); and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

Tablets:
mixing of active ingredient/s and auxiliaries, compression of said mixture into tablets (direct compression), optionally granulation of part of mixture before compression.

Capsules:
mixing of active ingredient/s and auxiliaries to obtain a flowable powder, optionally granulating powder, filling powders/granulate into opened capsules, capping of capsules.

Semi-Solids (Ointments, Gels, Creams):
dissolving/dispersing active ingredient/s in an aqueous or fatty carrier; subsequent mixing of aqueous/fatty phase with complementary fatty/aqueous phase, homogenization (creams only).

Suppositories (Rectal and Vaginal):
dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

Aerosols:
dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound according to this invention and one or more additional compounds other than the compounds according to the invention, which show valuable pharmaceutical properties, preferably those pharmaceutical active agents other than the compounds according to the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or Vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropymethyl-cellulose phthalate, are used Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The present invention includes within its scope prodrugs of the compounds of the present invention above. In general, such prodrugs will be functional derivatives of the compounds of the present invention, which are readily convertible in vivo into the required compound of the present invention. Conventional procedures for the selection and preparation of suitable prodrug derivatives are described, for example, in Design of Prodrugs, ed. H. Bundgaard, Elsevier, 1985.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds according to the invention is known to the skilled artisan or can be easily determined by standard methods known in the art.

The substances according to the invention are generally administered analogously to commercial preparations. Usually, suitable doses that are therapeutically effective lie in the range between 0.0005 mg and 1000 mg, preferably between 0.005 mg and 500 mg and especially between 0.5 and 100 mg per dose unit. The daily dose is preferably between about 0.001 and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The host, or patient, may be from any mammalian species, e.g., primate sp., particularly human; rodents, including mice, rats and hamsters; rabbits; equines, bovines, canines, felines; etc. Animal models are of interest for experimental investigations, providing a model for treatment of human disease.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated NaHCO$_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

Mass spectrometry (MS): ESI (electrospray ionisation) (M+H)$^+$

List of Abbreviations and Acronyms:

AcOH acetic acid, anh anhydrous, atm atmosphere(s), BOC tert-butoxycarbonyl CDI 1,1'-carbonyl diimidazole, conc concentrated, d day(s), dec decomposition, DMAC NN-dimethylacetamide, DMPU 1,3-dimethyl-3,4,5,6-tetrahydro-2(IH)-pyrimidinone, DMF NN-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylamine, h hour(s), MeOH methanol, pet. ether petroleum ether (boiling range 30-60° C.), temp. temperature, THF tetrahydrofuran, TFA trifluoroAcOH, Tf trifluoromethanesulfonyl.

The compounds of the present invention can be prepared by the general methods 1, 2 and 3 shown below. In all preparative methods, all starting material is known or may easily be prepared from known starting materials.

EXAMPLE 1

General Method 1

Synthesis of N-Adamantan-2yl-2-[1-(isobutylcarbamoyl-methyl)-cyclopentyl-acetamide and analogues

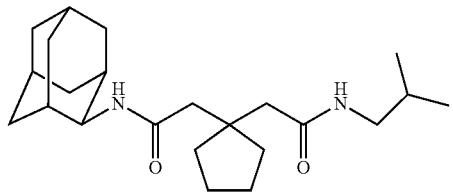

h 11β-HSD-1 IC50=9 nM

Step A: A mixture of 2-adamantylamine (2.8 g, 15 mmol), anhydride (3.0 g, 18 mmol) and triethylamine (2 ml, 15 mmol) in toluene (30 ml) was heated under reflux overnight. The reaction was concentrated and the residue filtered on a short bed of silica gel. The residue was triturated in Et$_2$O and the precipitate was filtered and dried under vacuum to give 4.8 g (69%) as a white solid.

HPLC-MS (M+H$^+$) 320.4

Step B: Isopropylamine (31 μl, 0.3 mmol) and HOBt (46 mg, 0.3 mmol) were added to a solution of the above prepared acid (100 mg, 0.3 mmol) in THF (1 ml). The mixture was cooled to −5° C. and a solution of DCC (64 mg, 0.3 mmol) in THF (1 ml) was added dropwise. The reaction mixture was stirred at rt overnight. The formed urea precipitate was filtered-off and the filtrate concentrated. The residue was purified by flash chromatography to give a white powder 117 mg (24%).

HPLC-MS (M+H$^+$) 375.5; $^1$H NMR (300 MHz, DMSO-d$_6$) δ ppm 8.40 (d, J=8 Hz, 1H) 8.17 (t, J=6 Hz, 1H), 3.89 (d, J=8 Hz, 1H), 2.93 (t, J=6 Hz, 2H), 2.25 (s, 2H), 2.23 (s, 2H), 1.95-1.41 (m, 22H), 0.86 (d, J=6.5 Hz, 6 H)

Examples Prepared by Method 1

| Examples | Mass (LCMS) |
| --- | --- |
| N-Adamantan-2yl-2-[1-(isobutylcarbamoyl-methyl)-cyclopentyl-acetamide | M + 1 = 375.3 |
| 4-(Adamantan-2-ylcarbamoyl)-3,3-dimethyl-butyric acid | M + 1 = 294.2 |
| [1-(Adamantan-2-ylcarbamoylmethyl)-cyclopentyl]-acetic acid | M + 1 = 320.1 |
| [1-(Adamantan-2-ylcarbamoylmethyl)-cyclohexyl]-acetic acid | M + 1 = 334.2 |
| 2-[1-(Adamantan-2-ylcarbamoylmethyl)-cyclopentyl]-N-(4-fluoro-phenyl)-acetamide | M + 1 = 413.3 |
| 2-[1-(Adamantan-2-ylcarbamoylmethyl)-cyclopentyl]-N-benzyl-N-methyl-acetamide | M + 1 = 423.4 |
| 2-[1-(Adamantan-2-ylcarbamoylmethyl)-cyclopentyl]-N-(2-methoxy-phenyl)-acetamide | M + 1 = 425.3 |
| 2-[1-(Adamantan-2-ylcarbamoylmethyl)-cyclopentyl]-N-(4-methoxy-phenyl)-acetamide | M + 1 = 425.3 |
| 2-[1-(Adamantan-2-ylcarbamoylmethyl)-cyclopentyl]-N-(4-fluoro-benzyl)-acetamide | M + 1 = 427.4 |
| 2-[1-(Adamantan-2-ylcarbamoylmethyl)-cyclopentyl]-N-pyridin-2-ylmethyl-acetamide | M + 1 = 410.3 |
| 2-[1-(Adamantan-2-ylcarbamoylmethyl)-cyclopentyl]-N-thiazol-2-yl-acetamide | M + 1 = 402.4 |
| 2-[1-(Adamantan-2-ylcarbamoylmethyl)-cyclopentyl]-N-isobutyl-acetamide | M + 1 = 375.4 |
| 2-[1-(Adamantan-2-ylcarbamoylmethyl)-cyclopentyl]-N-cyclopropyl-acetamide | M + 1 = 359.3 |
| N-Adamantan-2-yl-2-[1-(2-oxo-2-pyrrolidin-1-yl-ethyl)-cyclopentyl]-acetamide | M + 1 = 373.3 |
| {1-[(5-Hydroxy-adamantan-2-ylcarbamoyl)-methyl]-cyclohexyl}-acetic acid | M + 1 = 350.1 |
| 3,3-Dimethyl-pentanedioic acid adamantan-2-ylamide cyclopropylamide | M + 1 = 333.2 |
| 3,3-Dimethyl-5-(4-methyl-piperazin-1-yl)-5-oxo-pentanoic acid adamantan-2-ylamide | M + 1 = 376.3 |
| 5-(4-Ethyl-piperazin-1-yl)-3,3-dimethyl-5-oxo-pentanoic acid adamantan-2-ylamide | M + 1 = 390.2 |
| 3,3-Dimethyl-pentanedioic acid adamantan-2-ylamide piperidin-1-ylamide | M + 1 = 376.3 |
| N-Adamantan-2-yl-2-{1-[2-(4-methyl-piperazin-1-yl)-2-oxo-ethyl]-cyclohexyl}-acetamide | M + 1 = 416.1 |
| N-Adamantan-2-yl-2-{1-[2-(4-ethyl-piperazin-1-yl)-2-oxo-ethyl]-cyclohexyl}-acetamide | M + 1 = 430.2 |
| N-Adamantan-2-yl-2-{1-[2-(4-methyl-piperazin-1-yl)-2-oxo-ethyl]-cyclopentyl}-acetamide | M + 1 = 402.2 |
| N-Adamantan-2-yl-2-{1-[2-(4-ethyl-piperazin-1-yl)-2-oxo-ethyl]-cyclopentyl}-acetamide | M + 1 = 416.3 |
| N-Adamantan-2-yl-2-[1-(piperidin-1-ylcarbamoylmethyl)-cyclopentyl]-acetamide | M + 1 = 402.2 |
| 2-(1-Cyclopropylcarbamoylmethyl-cyclopentyl)-N-(5-hydroxy-adamantan-2-yl)-acetamide | M + 1 = 375.2 |
| 2-(1-Cyclopropylcarbamoylmethyl-cyclopentyl)-N-(5-hydroxy-adamantan-2-yl)-acetamide | M + 1 = 376.3 |
| N-Adamantan-2-yl-2-(1-cyclopropylcarbamoylmethyl-cyclohexyl)-acetamide | M + 1 = 373.3 |
| 3,3-Dimethyl-5-((S)-3-methyl-piperidin-1-yl)-5-oxo-pentanoic acid adamantan-2-ylamide | M + 1 = 375.1 |
| 3,3-Dimethyl-5-((R)-3-methyl-piperidin-1-yl)-5-oxo-pentanoic acid adamantan-2-ylamide | M + 1 = 375.1 |
| N-Adamantan-2-yl-2-{1-[2-((S)-3-methyl-piperidin-1-yl)-2-oxo-ethyl]-cyclopentyl}-acetamide | M + 1 = 401.3 |
| N-Adamantan-2-yl-2-{1-[2-((R)-3-methyl-piperidin-1-yl)-2-oxo-ethyl]-cyclopentyl}-acetamide | M + 1 = 401.3 |
| N-Adamantan-2-yl-2-{1-[2-((S)-3-methyl-piperidin-1-yl)-2-oxo-ethyl]-cyclohexyl}-acetamide | M + 1 = 415.3 |

| Examples | Mass (LCMS) |
| --- | --- |
| N-Adamantan-2-yl-2-{1-[2-((R)-3-methyl-piperidin-1-yl)-2-oxo-ethyl]-cyclohexyl}-acetamide | M + 1 = 415.3 |
| 3,3-Dimethyl-pentanedioic acid cyclopropylamide (5-hydroxy-adamantan-2-yl)-amide | M + 1 = 349.2 |

EXAMPLE 2

General Method 2

Synthesis of N-Adamantan-2-yl-4-(4-chloro-2-methoxy-phenoxy)-3,3-dimethyl-butyramide and analogues

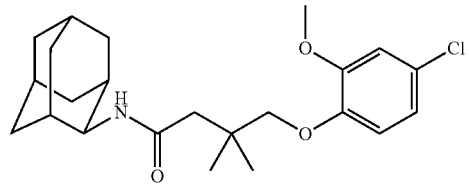

h-11β-HSD-1 IC50=45 nM

Step A: A mixture of phenol (65 g, 0.4 mol) and NaOH (16 g, 0.4 mol) in 1-butanol (160 g) was stirred at 130-140° C. and butanol/H$_2$O distilled off. The lactone (62.4 g, 0.54 mol) was added at once. The temperature was raised to 160-170° C. for 10 h. After cooling to 80° C., water was added followed by the addition of 1N HCl. The reaction mixture was extracted with DCM and the organic layer was washed with water, dried over Na$_2$SO$_4$ and concentrated. The brown residue was distilled under vacuum to yield a yellow oil which crystallize on standing (110 g, 33%).

Step B: A solution of DCC (166 mg, 0.80 mmol) in THF (1 ml) was added dropwise to a mixture of 2-adamantylamine (151 mg, 0.80 mmol), the carboxylic acid (200 mg, 0.73 mmol), HOBt (108 mg, 0.8 mmol) and triethylamine (110 μl, 0.80 mmol) in THF (3 ml). The reaction mixture was stirred at rt overnight and filtered. The filtrate was concentrated and the residue dissolved in EtOAc. The EtOAc solution was washed with 1N NaOH solution, water, brine, dried over Na$_2$SO$_4$ and concentrated. The residue was purified by flash chromatography to give a white powder (297 mg, 64%).

HPLC-MS (M+H$^+$) 406.9; $^1$H NMR (300 MHz, DMSO-d$_6$) δ ppm 7.60 (d, J=6 Hz, 1H), 7.00 (d, J=2 Hz, 1H), 6.90 (m, 2H), 3.85 (d, J=7 Hz, 1H), 3.80 (s, 3H), 3.77 (s, 2H), 2.25 (s, 2H), 1.98-1.46 (m, 14H), 1.06 (s, 6H)

Examples Prepared by Method 2

| Examples | Mass (LCMS) |
| --- | --- |
| N-Adamantan-2-yl-4-(4-chloro-2-methoxy-phenoxy)-3,3-dimethyl-butyramide | M + 1 = 406.1 |
| N-Adamantan-2-yl-4-(2-chloro-phenoxy)-3,3-dimethyl-butyramide | M + 1 = 376.1 |
| N-Adamantan-2-yl-4-(2,4-dichloro-phenoxy)-3,3-dimethyl-butyramide | M + 1 = 410.1 |

EXAMPLE 3

General Method 3

Synthesis of N-Adamantan-2-yl-3,3-dimethyl-4-(3-pyridin-2-yl-[1,2,4]oxadiazol-5yl)-butyramide and analogues

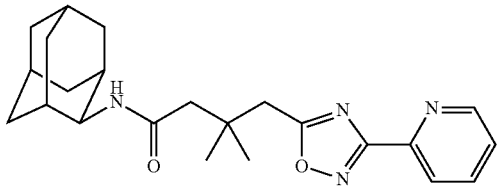

h-11β-HSD-1 IC50=57 nM

Step A: HOBt (110 mg, 0.8 mmol) and DCC (168 mg, 0.8 mmol) were added to a solution of acide (200 mg, 0.6 mmol) and amidoxime (69 mg, 0.6 mmol) in a mixture of solvents DCM/DMF (9/1) (3.3 ml) at −10° C. The reaction was stirred at −10° C. for 20 min and 2 h at rt. Solvents were removed by vacuum, EtOAc added to the residue and the resulting precipitate was filtered off. The organic filtrate was washed with a solution of NaHCO$_3$, water, a solution of NaHSO$_4$ 0.5 N, brine, dried over MgSO$_4$ and concentrated.

HPLC-MS (M+H$^+$) 413.5

Step B: A solution of acylamidoxime (185 mg, 0.49 mmol) in DMF (3 ml) was heated at 110° C. for 48 h. The reaction was quenched with water and extracted with EtOAc, washed with water and concentrated. The residue was purified by preparative LCMS to give 5 mg (2.8%) as a white powder.

HPLC-MS (M+H$^+$) 395.5; $^1$H NMR (300 MHz, DMSO-d$_6$) δ ppm 8.78 (d, J=4 Hz, 1H), 8.11-8.04 (m, 2H), 7.74 (d, J=8 Hz, 1H), 7.62 (m, 1H), 3.89 (d, J=7 Hz, 1H), 3.15 (s, 2H), 2.28 (s, 2H), 2.02-1.48 (m, 14H), 1.10 (s, 6H)

Examples Prepared by Method 3

| Examples | Mass (LCMS) |
|---|---|
| N-Adamantan-2-yl-4-(3-cyclopropyl-[1,2,4]oxadiazol-5-yl)-3,3-dimethyl-butyramide | M + 1 = 358.2 |
| N-Adamantan-2-yl-4-(3-isopropyl-[1,2,4]oxadiazol-5-yl)-3,3-dimethyl-butyramide | M + 1 = 360.2 |
| N-Adamantan-2-yl-3,3-dimethyl-4-(3-pyridin-2-yl-[1,2,4]oxadiazol-5-yl)-butyramide | M + 1 = 395.2 |
| N-Adamantan-2-yl-3,3-dimethyl-4-(3-m-tolyl-[1,2,4]oxadiazol-5-yl)-butyramide | M + 1 = 408.2 |
| N-Adamantan-2-yl-3,3-dimethyl-4-(3-p-tolyl-[1,2,4]oxadiazol-5-yl)-butyramide | M + 1 = 408.2 |
| N-Adamantan-2-yl-4-[3-(4-methoxy-phenyl)-[1,2,4]oxadiazol-5-yl]-3,3-dimethyl-butyramide | M + 1 = 424.2 |
| N-Adamantan-2-yl-4-[3-(4-chloro-phenyl)-[1,2,4]oxadiazol-5-yl]-3,3-dimethyl-butyramide | M + 1 = 428.2 |
| N-Adamantan-2-yl-2-[1-(3-cyclopropyl-[1,2,4]oxadiazol-5-ylmethyl)-cyclopentyl]-acetamide | M + 1 = 384.3 |
| N-Adamantan-2-yl-2-[1-(3-isopropyl-[1,2,4]oxadiazol-5-ylmethyl)-cyclopentyl]-acetamide | M + 1 = 386.3 |
| N-Adamantan-2-yl-2-[1-(3-pyridin-2-yl-[1,2,4]oxadiazol-5-ylmethyl)-cyclopentyl]-acetamide | M + 1 = 421.3 |
| N-Adamantan-2-yl-2-[1-(3-m-tolyl-[1,2,4]oxadiazol-5-ylmethyl)-cyclopentyl]-acetamide | M + 1 = 434.4 |
| N-Adamantan-2-yl-2-[1-(3-p-tolyl-[1,2,4]oxadiazol-5-ylmethyl)-cyclopentyl]-acetamide | M + 1 = 434.4 |
| N-Adamantan-2-yl-2-{1-[3-(4-methoxy-phenyl)-[1,2,4]oxadiazol-5-ylmethyl]-cyclopentyl}-acetamide | M + 1 = 450.3 |

EXAMPLE 4

Assays—Measurement of Inhibition Constants

Human recombinant 11beta-hydroxysteroid dehydrogenase type 1 (11beta-HSD1) enzyme was expressed in *E. Coli*. Mice liver microsome fractions were purchased from TEBU.

The 11beta-HSD1 enzyme assay was carried out in 96 well microtiter plates in a total volume of 100 μl containing 30 mM Hepes buffer, pH 7.4 with 1 mM EDTA, substrate mixture cortisone/NADPH (200 nM/200 μM), G-6-P (1 mM) and inhibitors in serial dilutions. Reactions were initiated by addition of 10 μl 11beta-HSD1 (3 μg) from *E. Coli*, or as microsome fractions from mice liver (2.5 μg). Following mixing, the plates were shaken for 150 minutes at 37° C. The reactions were terminated with 10 μl Acid-18beta glycyrrhetinic stop solution. Determinations of cortisol levels in 11 beta-HSD1 preparations were monitored by HTRF (HTRF cortisol assay from Cis bio international).

Activity is expressed in % of control or concentration to inhibit 50% of the enzyme activity (IC50).

N-Adamantan-2yl-2-[1-(isobutylcarbamoyl-methyl)-cyclopentyl-acetamide: h-11β-HSD-1 IC50=9 nM N-Adamantan-2-yl-4-(4-chloro-2-methoxy-phenoxy)-3,3-dimethyl-butyramide: h-11β-HSD-1 IC50=45 nM N-Adamantan-2-yl-3,3-dimethyl-4-(3-pyridin-2-yl-[1,2,4]oxadiazol-5yl)-butyramide: h-11β-HSD-1 IC50=57 nM N-Adamantan-2-yl-4-(3-isopropyl-[1,2,4]oxadiazol-5-yl)-3,3-dimethyl-butyramide: h 11β-HSD-1 IC50=9 nM

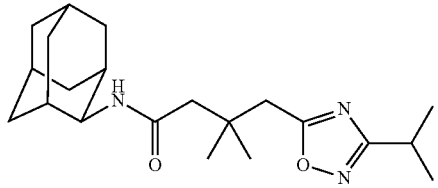

EXAMPLE 5

Injection Vials

A solution of 100 g of an active compound of the present invention and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

EXAMPLE 6

Suppositories

A mixture of 20 g of an active compound of the present invention is fused with 100 g of soya lecithin and 1400 g of cocoa butter, poured into moulds and allowed to cool. Each suppository contains 20 mg of active compound.

EXAMPLE 7

Solution

A solution of 1 g of an active compound of the present invention, 9.38 g of NaH$_2$PO$_4$.2H$_2$O, 28.48 g of $Na_2HPO_4.12H_2O$ and 0.1 g of benzalkonium chloride in 940 ml of double-distilled water is prepared. It is adjusted to pH 6.8, made up to 1 l and sterilized by irradiation. This solution can be used in the form of eye drops.

EXAMPLE 8

Ointment 500 mg of an active compound of the present invention is mixed with 99.5 g of petroleum jelly under aseptic conditions.

EXAMPLE 9

Tablets

A mixture of 1 kg of an active compound of the present invention, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE 10

Coated Tablets

Analogously to the previous example, tablets are pressed and are then coated in a customary manner using a coating of sucrose, potato starch, talc, tragacanth and colourant.

EXAMPLE 12

Capsules 2 kg of an active compound of the present invention are dispensed into hard gelatin capsules in a customary manner such that each capsule contains 20 mg of the active compound.

The invention claimed is:
1. Compound of the formula I

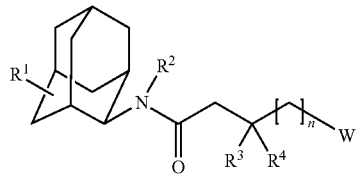

I wherein, the adamantyl residue is mono-, di- or trisubstituted by $R^1$ and
$R^1$ is H, A, Ar, heteroaryl, cycloalkyl, alkyloxy, aryloxy, Hal, $OR^7$, $SR^7$, $N(R^7)_2$, $NO_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, COAr, $SO_2NH_2$, $OSO_3R^7$, $SO_2R^7$, $SO_3R^7$, $SO_2N(R^7)_2$, $OCOR^7$ or $OCON(R^7)_2$,
$R^2$ is H or A,
$R^3$, $R^4$ are independently from each other H, Hal, $C_1$-$C_4$-alkyl or $C_1$-$C_4$-alkyloxy, or $R^3$, $R^4$ and the C to which they are attached form a $C_3$-$C_9$-cycloalkyl or a $C_3$-$C_9$-cycloalkyloxy, and $R^3$, $R^4$ or the cycloalkyl or cycloalkyloxy ring are optionally mono-, di- or trisubstituted by $R^5$ or $R^6$,
W is oxadiazolyl or phenoxy, optionally mono-, di- or trisubstituted by $R^5$ or $R^6$ or W is $CONR^5R^6$, $R^5$, $R^6$ are independently from each other H, A, Ar, heteroaryl, cycloalkyl, alkyloxy, aryloxy, Hal, $OR^7$, $SR^7$, $N(R^7)_2$, $NO_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, COAr, $SO_2NH_2$, $OSO_3R^7$, $SO_2R^7$, $SO_3R^7$ or $SO_2N(R^7)_2$,
$R^7$ is H or alkyl, wherein optionally 1-7H-atoms are substituted by Hal,
A is alkyl, cycloalkyl or cycloalkylalkyl,
n is 1 or 2, and
m 0, 1, 2, 3, 4 or 5,
and the physiologically acceptable salts and stereoisomers thereof, including mixtures thereof in all ratios.
2. Compound according to claim 1, wherein W is oxadiazolyl or phenoxy substituted by $R^5$ and $R^6$,
and the physiologically acceptable salts and stereoisomers thereof, including mixtures thereof in all ratios.
3. Compound according to claim 1, wherein $R^3$, $R^4$ are independently from each other Hal or methyl, or $R^3$, $R^4$ and the C to which they are attached form a cyclopentyl or cyclohexyl,
and the physiologically acceptable salts and stereoisomers thereof, including mixtures thereof in all ratios.
4. Compound according to claim 1, wherein $R^1$ is H, Hal, $OR^7$, $SR^7$, $N(R^7)_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $SO_2NH_2$, $OSO_3R^7$, $SO_2R^7$, $SO_3R^7$, $SO_2N(R^7)_2$, $OCOR^7$ or $OCON(R^7)_2$,
and the physiologically acceptable salts and stereoisomers thereof, including mixtures thereof in all ratios.
5. Compound according to claim 1, $R^2$ is H or Me, and the physiologically acceptable salts and stereoisomers thereof, including mixtures thereof in all ratios.
6. Compound according to claim 1, wherein
$R^1$ is H, Hal, $OR^7$, $SR^7$, $N(R^7)_2$, CN, $(CH_2)_mCOOR^7$, $(CH_2)_mCON(R^7)_2$, $NR^7COR^7$, $NR^7CON(R^7)_2$, $NR^7SO_2R^7$, $COR^7$, $SO_2NH_2$, $OSO_3R^7$, $SO_2R^7$, $SO_3R^7$, $SO_2N(R^7)_2$, $OCOR^7$ or $OCON(R^7)_2$,
$R^2$ is H or Me,
$R^3$, $R^4$ are independently from each other Hal or methyl, or $R^3$, $R^4$ and the C to which they are attached form a cyclopentyl or cyclohexyl,
W is $CONR^5R^6$, oxadiazolyl or phenoxy substituted by $R^5$ and $R^6$,
and the physiologically acceptable salts and stereoisomers thereof, including mixtures thereof in all ratios.
7. Compound selected from the group consisting of
a) N-Adamantan-2-yl-2-[1-(isobutylcarbamoyl-methyl)-cyclopentyl-acetamide
b) 4-(Adamantan-2-ylcarbamoyl)-3,3-dimethyl-butyric acid
c) [1-(Adamantan-2-ylcarbamoylmethyl)-cyclopentyl]-acetic acid
d) [1-(Adamantan-2-ylcarbamoylmethyl)-cyclohexyl]-acetic acid
e) 2-[1-(Adamantan-2-ylcarbamoylmethyl)-cyclopentyl]-N-(4-fluoro-phenyl)-acetamide
f) 2-[1-(Adamantan-2-ylcarbamoylmethyl)-cyclopentyl]-N-benzyl-N-methyl-acetamide
g) 2-[1-(Adamantan-2-ylcarbamoylmethyl)-cyclopentyl]-N-(2-methoxy-phenyl)-acetamide
h) 2-[1-(Adamantan-2-ylcarbamoylmethyl)-cyclopentyl]-N-(4-methoxy-phenyl)-acetamide
i) 2-[1-(Adamantan-2-ylcarbamoylmethyl)-cyclopentyl]-N-(4-fluoro-benzyl)-acetamide
j) 2-[1-(Adamantan-2-ylcarbamoylmethyl)-cyclopentyl]-N-pyridin-2-ylmethyl-acetamide k) 2-[1-(Adamantan-2-ylcarbamoylmethyl)-cyclopentyl]-N-thiazol-2-yl-acetamide
l) 2-[1-(Adamantan-2-ylcarbamoylmethyl)-cyclopentyl]-N-isobutyl-acetamide
m) 2-[1-(Adamantan-2-ylcarbamoylmethyl)-cyclopentyl]-N-cyclopropyl-acetamide
n) N-Adamantan-2-yl-2-[1-(2-oxo-2-pyrrolidin-1-yl-ethyl)-cyclopentyl]-acetamide
o) {1-[(5-Hydroxy-adamantan-2-ylcarbamoyl)-methyl]-cyclohexyl}-acetic acid
p) 3,3-Dimethyl-pentanedioic acid adamantan-2-ylamide cyclopropylamide
q) 3,3-Dimethyl-5-(4-methyl-piperazin-1-yl)-5-oxo-pentanoic acid adamantan-2-ylamide
r) 5-(4-Ethyl-piperazin-1-yl)-3,3-dimethyl-5-oxo-pentanoic acid adamantan-2-ylamide
s) 3,3-Dimethyl-pentanedioic acid adamantan-2-ylamide piperidin-1-ylamide
t) N-Adamantan-2-yl-2-{1-[2-(4-methyl-piperazin-1-yl)-2-oxo-ethyl]-cyclohexyl}-acetamide
u) N-Adamantan-2-yl-2-{1-[2-(4-ethyl-piperazin-1-yl)-2-oxo-ethyl]-cyclohexyl}-acetamide
v) N-Adamantan-2-yl-2-{1-[2-(4-methyl-piperazin-1-yl)-2-oxo-ethyl]-cyclopentyl}-acetamide
w) N-Adamantan-2-yl-2-{1-[2-(4-ethyl-piperazin-1-yl)-2-oxo-ethyl]-cyclopentyl}-acetamide
x) N-Adamantan-2-yl-2-[1-(piperidin-1-ylcarbamoylmethyl)-cyclopentyl]-acetamide
y) 2-(1-Cyclopropylcarbamoylmethyl-cyclopentyl)-N-(5-hydroxy-adamantan-2-yl)-acetamide
z) 2-(1-Cyclopropylcarbamoylmethyl-cyclopentyl)-N-(5-hydroxy-adamantan-2-yl)-acetamide
aa) N-Adamantan-2-yl-2-(1-cyclopropylcarbamoylmethyl-cyclohexyl)-acetamide
bb) 3,3-Dimethyl-5-((S)-3-methyl-piperidin-1-yl)-5-oxo-pentanoic acid adamantan-2-ylamide
cc) 3,3-Dimethyl-5-((R)-3-methyl-piperidin-1-yl)-5-oxo-pentanoic acid adamantan-2-ylamide
dd) N-Adamantan-2-yl-2-{1-[2-((S)-3-methyl-piperidin-1-yl)-2-oxo-ethyl]-cyclopentyl}-acetamide
ee) N-Adamantan-2-yl-2-{1-[2-((R)-3-methyl-piperidin-1-yl)-2-oxo-ethyl]-cyclopentyl}-acetamide
ff) N-Adamantan-2-yl-2-{1-[2-((S)-3-methyl-piperidin-1-yl)-2-oxo-ethyl]-cyclohexyl}-acetamide
gg) N-Adamantan-2-yl-2-{1-[2-((R)-3-methyl-piperidin-1-yl)-2-oxo-ethyl]-cyclohexyl}-acetamide
hh) 3,3-Dimethyl-pentanedioic acid cyclopropylamide(5-hydroxy-adamantan-2-yl)-amide
ii) N-Adamantan-2-yl-4-(4-chloro-2-methoxy-phenoxy)-3,3-dimethyl-butyramide
jj) N-Adamantan-2-yl-4-(2-chloro-phenoxy)-3,3-dimethyl-butyramide
kk) N-Adamantan-2-yl-4-(2,4-dichloro-phenoxy)-3,3-dimethyl-butyramide
ll) N-Adamantan-2-yl-4-(3-cyclopropyl-[1,2,4]oxadiazol-5-yl)-3,3-dimethyl-butyramide
mm) N-Adamantan-2-yl-4-(3-isopropyl-[1,2,4]oxadiazol-5-yl)-3,3-dimethyl-butyramide
nn) N-Adamantan-2-yl-3,3-dimethyl-4-(3-pyridin-2-yl-[1,2,4]oxadiazol-5-yl)-butyramide
oo) N-Adamantan-2-yl-3,3-dimethyl-4-(3-m-tolyl-[1,2,4]oxadiazol-5-yl)-butyramide
pp) N-Adamantan-2-yl-3,3-dimethyl-4-(3-p-tolyl-[1,2,4]oxadiazol-5-yl)-butyramide
qq) N-Adamantan-2-yl-4-[3-(4-methoxy-phenyl)-[1,2,4]oxadiazol-5-yl]-3,3-dimethyl-butyramide
rr) N-Adamantan-2-yl-4-[3-(4-chloro-phenyl)-[1,2,4]oxadiazol-5-yl]-3,3-dimethyl-butyramide
ss) N-Adamantan-2-yl-2-[1-(3-cyclopropyl-[1,2,4]oxadiazol-5-ylmethyl)-cyclopentyl]-acetamide
tt) N-Adamantan-2-yl-2-[1-(3-isopropyl-[1,2,4]oxadiazol-5-ylmethyl)-cyclopentyl]-acetamide
uu) N-Adamantan-2-yl-2-[1-(3-pyridin-2-yl-[1,2,4]oxadiazol-5-ylmethyl)-cyclopentyl]-acetamide
vv) N-Adamantan-2-yl-2-[1-(3-m-tolyl-[1,2,4]oxadiazol-5-ylmethyl)-cyclopentyl]-acetamide
ww) N-Adamantan-2-yl-2-[1-(3-p-tolyl-[1,2,4]oxadiazol-5-ylmethyl)-cyclopentyl]-acetamide
xx) N-Adamantan-2-yl-2-{1-[3-(4-methoxy-phenyl)-1,2,4]oxadiazol-5-ylmethyl]-cyclopentyl}-acetamide and the physiologically acceptable salts and stereoisomers thereof, including mixtures thereof in all ratios.

8. Method for the preparation of a compound according to claim 1, characterized in that a) an amine of formula II, wherein $R^1$ and $R^2$ are as defined above, is reacted with an anhydride of formula III, wherein $R^3$ and $R^4$ are as defined above, to obtain a carboxylic acid derivative of formula IV, wherein $R^1$, $R^2$, $R^3$ and $R^4$ are as defined above, and to activate said carboxylic acid derivative with standard carbodiimides, followed by treatment with an amine of formula V, wherein $R^5$ and $R^6$ are as defined above,

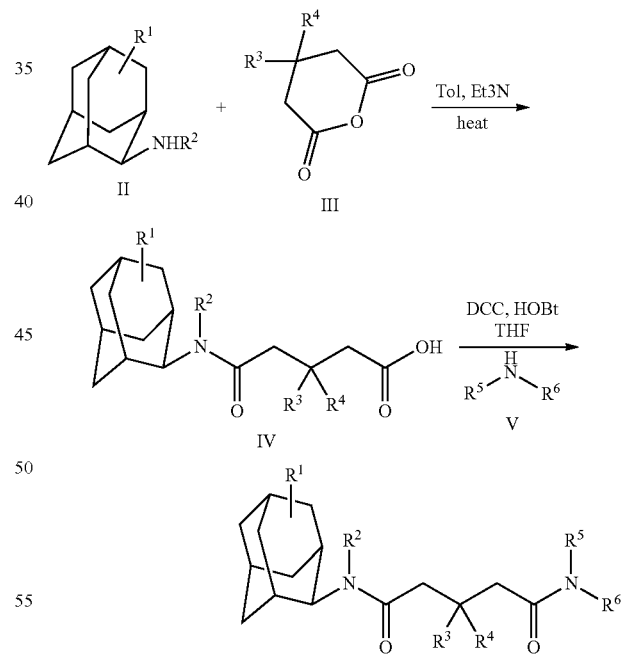

b) a phenol derivative of formula VI, wherein $R^5$ and $R^6$ are as defined above, is reacted with a lactone of formula VII, wherein $R^3$ and $R^4$ are as defined above, under heat to obtain a carboxylic acid derivative of formula IV, wherein $R^3$, $R^4$, $R^5$ and $R^6$ are as defined above, and the respective compound of formula I, wherein $R^1$, $R^2$, $R^3$, $R^4$, $R^5$ and $R^6$ are as defined above, is obtain by amide coupling under standard peptide coupling conditions,

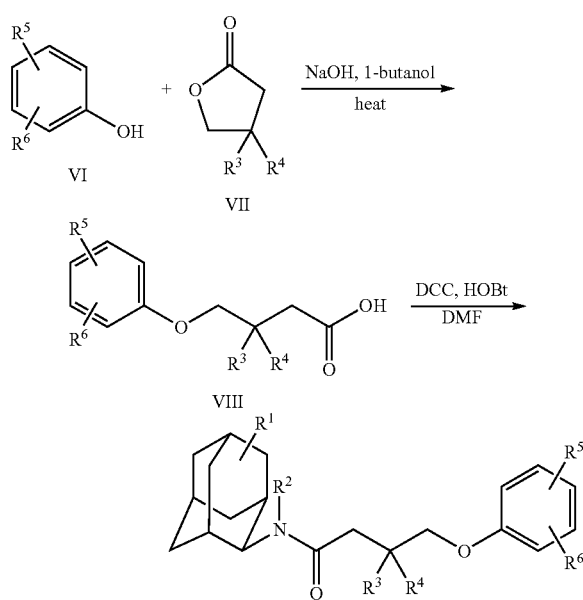

c) a carboxylic acid of formula IV, wherein $R^1$, $R^2$, $R^3$ and $R^4$ are as defined above, is activated and reacted with an amidoxime of formula IX, wherein $R^5$ is as defined above, to obtain an acylamidoxamine of formula X, wherein $R^1$, $R^2$, $R^3$, $R^4$ and $R^5$ are as defined above, and cyclization to a oxadiazole of formula XI, wherein $R^1$, $R^2$, $R^3$, $R^4$ and $R^5$ are as defined above, is obtained by heating said acylamidoxamine in DMF,

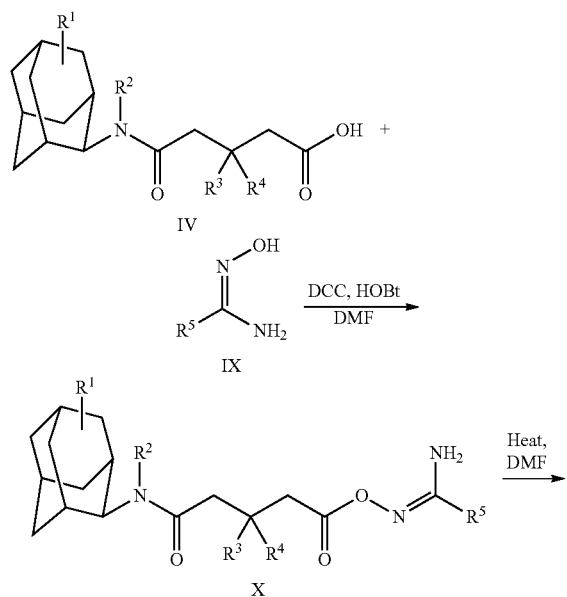

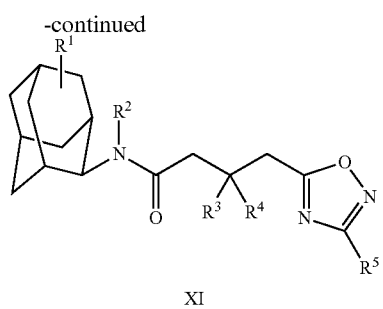

d) a residue $R^1$, $R^2$, $R^3$, $R^4$, $R^5$, $R^6$ and/or $R^7$ as defined in claim 1, is converted in another residue $R^1$, $R^2$, $R^3$, $R^4$, $R^5$, $R^6$ and/or $R^7$, e.g. by introducing an alkyl group, or e) a compound of formula I is isolated and/or treated with an acid or a base, to obtain the salt thereof.

9. A method for the treatment of one or more disease or condition selected from the group consisting of metabolic syndrome, diabetes, insulin resistance, glucose intolerance, obesity, dyslipidemia, hyperlipidemia, hypertriglyceridemia, hypercholesterolemia, low HDL levels or high LDL levels, glaucoma, osteoporosis, glucocorticoid-mediated effects on neuronal function, cognitive impairment, anxiety, depression, tuberculosis, leprosy, psoriasis, hypertension, atherosclerosis, and Cushing's syndrome, by administering to a patient a compound of claim 1 to effect 11β-HSD1 inhibition.

10. Pharmaceutical composition, characterized in that it contains a therapeutically effective amount of one or more compounds according to claim 1.

11. Pharmaceutical composition according to claim 10, characterized in that it contains one or more additional compounds, selected from the group consisting of physiologically acceptable excipients, auxiliaries, adjuvants, diluents, carriers and pharmaceutically active agents.

12. Set (kit) consisting of separate packets of a) a therapeutically effective amount of one or more compounds according to claim 1 and b) a therapeutically effective amount of one or more further pharmaceutically active agents other than the compounds according to claim 1.

13. Process for the manufacture of a pharmaceutical composition, characterized in that one or more compounds according to claim 1 and one or more compounds selected from the group consisting of solid, liquid or semiliquid excipients, auxiliaries, adjuvants, diluents, carriers and pharmaceutically active agents other than the compounds according to claim 1, are converted in a suitable dosage form.

14. A compound according to claim 1, wherein W is $CONR^5R^6$ and the physiologically acceptable salts and stereoisomers thereof, including mixtures thereof in all ratios.

* * * * *